United States Patent
Ramachandran et al.

(10) Patent No.: US 10,925,705 B2
(45) Date of Patent: Feb. 23, 2021

(54) PESSARY WITH APPLICATOR

(71) Applicant: The Procter & Gamble Company, Cincinnati, OH (US)

(72) Inventors: Alexzandra Joan Ramachandran, Cincinnati, OH (US); Robert Clark Avery, Jr., Mason, OH (US); Nancy Karapasha, Cleves, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 127 days.

(21) Appl. No.: 16/227,763

(22) Filed: Dec. 20, 2018

(65) Prior Publication Data

US 2019/0125510 A1 May 2, 2019

Related U.S. Application Data (63) Continuation of application No. 15/194,909, filed on Jun. 28, 2016, now Pat. No. 10,201,411.

(60) Provisional application No. 62/185,911, filed on Jun. 19, 2015.

(51) Int. Cl.
| | |
|---|---|
| *A61F 2/00* | (2006.01) |
| *A61F 6/12* | (2006.01) |
| *A61F 6/08* | (2006.01) |
| *A61F 13/26* | (2006.01) |

(52) U.S. Cl.
CPC .............. *A61F 2/005* (2013.01); *A61F 6/08* (2013.01); *A61F 6/12* (2013.01); *A61F 13/26* (2013.01); *A61F 2250/0078* (2013.01)

(58) Field of Classification Search
CPC .... A61F 6/08; A61F 2250/0078; A61F 13/26; A61F 2/005; A61F 6/12
USPC ..................................................... 600/29–32
See application file for complete search history.

(56) References Cited

U.S. PATENT DOCUMENTS

| | | |
|---|---|---|
| 395,005 A | 12/1888 | Sharp |
| 404,019 A | 5/1889 | Sperry |
| 525,785 A | 9/1894 | Hurdle |
| 748,650 A | 1/1904 | Priest |
| 1,222,825 A | 4/1917 | Walter |
| 2,049,270 A | 7/1936 | Munro |
| 2,092,427 A | 9/1937 | Alexnader |
| 2,457,349 A | 12/1948 | Clark |
| 2,922,422 A | 1/1960 | Bletzinger |

(Continued)

FOREIGN PATENT DOCUMENTS

| | | |
|---|---|---|
| FR | 611889 A | 10/1926 |
| JP | 2009232987 A1 | 10/2009 |

(Continued)

OTHER PUBLICATIONS

13915 PCT International Search Report and Written Opinion, dated Oct. 25, 2016 (9 pages).

*Primary Examiner* — Navin Natnithithadha
*Assistant Examiner* — Sunita Reddy
(74) *Attorney, Agent, or Firm* — William E. Gallagher (57) ABSTRACT

An intravaginal pessary device in an applicator is provided. The device has a top and a bottom, and a sidewall that extends between the top and the bottom. The sidewall, top and bottom form an outer periphery defining a total area of the device. The pessary device has a maximum diameter that is less than about 25 mm. The pessary device and applicator exhibit a maximum expulsion force that is below 1500 grams.

11 Claims, 8 Drawing Sheets

(56) References Cited

U.S. PATENT DOCUMENTS

| | | | |
|---|---|---|---|
| 2,922,423 A | 1/1960 | Rickard | |
| 3,358,686 A | 12/1967 | Kunitami | |
| 3,452,752 A | 7/1969 | Crescenzo | |
| 3,749,093 A | 7/1973 | Bloom | |
| 4,019,498 A | 4/1977 | Hawtrey et al. | |
| 4,307,716 A | 12/1981 | Davis | |
| 4,610,659 A | 9/1986 | Friese | |
| 5,135,475 A | 8/1992 | Nakanishi | |
| 5,346,468 A | 9/1994 | Campion | |
| 5,558,631 A | 9/1996 | Campion | |
| 5,618,256 A * | 4/1997 | Reimer | A61F 2/005 600/29 |
| 5,785,640 A * | 7/1998 | Kresch | A61F 2/005 600/29 |
| 6,019,744 A | 2/2000 | Altdorf | |
| 6,090,038 A * | 7/2000 | Zunker | A61F 13/2065 600/29 |
| 6,165,108 A * | 12/2000 | Ralston | A63B 23/20 482/105 |
| 6,450,986 B1 | 9/2002 | Binner | |
| 6,503,190 B1 | 1/2003 | Ulmsten et al. | |
| 6,739,340 B1 | 5/2004 | Jensen et al. | |
| 6,770,025 B2 | 8/2004 | Zunker | |
| 6,808,485 B2 | 10/2004 | Zunker | |
| 6,958,057 B2 | 10/2005 | Berg, Jr. | |
| 7,351,195 B2 | 4/2008 | Farrell | |
| 7,717,892 B2 | 5/2010 | Bartning et al. | |
| 7,771,344 B2 | 8/2010 | Ziv | |
| 8,870,724 B2 | 10/2014 | Armitage et al. | |
| 2002/0120243 A1 | 8/2002 | Kraemer et al. | |
| 2003/0028176 A1 | 2/2003 | Berg et al. | |
| 2003/0176844 A1* | 9/2003 | Randall | A61F 13/2051 604/385.17 |
| 2004/0249238 A1* | 12/2004 | Farrell | A61F 2/005 600/29 |
| 2005/0113781 A1* | 5/2005 | Forgeot | A61F 2/005 604/385.18 |
| 2005/0148995 A1 | 7/2005 | Shepard et al. | |
| 2006/0111661 A1 | 5/2006 | Gann et al. | |
| 2006/0155240 A1 | 7/2006 | Osborn, III et al. | |
| 2006/0161096 A1 | 7/2006 | Osborn, III et al. | |
| 2007/0027667 A1 | 2/2007 | Osborn, III | |
| 2007/0203429 A1* | 8/2007 | Ziv | A61F 2/005 600/573 |
| 2007/0244352 A1 | 10/2007 | Ziv | |
| 2008/0009614 A1 | 1/2008 | Bartning | |
| 2008/0108861 A1 | 5/2008 | Harris et al. | |
| 2008/0167599 A1* | 7/2008 | Osborn | A61F 13/266 604/14 |
| 2008/0195030 A1* | 8/2008 | Gann | A61F 13/26 604/15 |
| 2008/0214984 A1* | 9/2008 | Caracci | A61F 13/8405 604/12 |
| 2008/0254441 A1 | 10/2008 | Mohammed et al. | |
| 2009/0095304 A1* | 4/2009 | Richardson | A61F 2/0009 128/834 |
| 2009/0203959 A1* | 8/2009 | Ziv | A61F 2/0009 600/29 |
| 2009/0266367 A1* | 10/2009 | Ziv | A61F 2/005 128/834 |
| 2010/0000897 A1* | 1/2010 | Bumpass | A61F 15/003 206/440 |
| 2010/0145137 A1* | 6/2010 | Morgan | A63B 23/20 600/29 |
| 2011/0060548 A1 | 3/2011 | Hill | |
| 2011/0105830 A1* | 5/2011 | Hou | A61F 13/2097 600/30 |
| 2012/0165599 A1* | 6/2012 | Ellefson | A61F 13/202 600/29 |
| 2012/0165601 A1* | 6/2012 | Ellefson | A61F 13/2071 600/30 |
| 2012/0259161 A1 | 10/2012 | Karapasha | |
| 2013/0053627 A1* | 2/2013 | Bercovich | A61F 2/005 600/31 |

FOREIGN PATENT DOCUMENTS

| | | |
|---|---|---|
| WO | WO9413223 A1 | 6/1994 |
| WO | WO9610965 A1 | 4/1996 |
| WO | WO2008063085 A1 | 5/2008 |

* cited by examiner

PESSARY WITH APPLICATOR

CROSS REFERENCE TO RELATED APPLICATION

This application is a continuation of application Ser. No. 15/194,909, filed Jun. 28, 2016; which claims the benefit of U.S. Provisional Application No. 62/185,911, filed Jun. 29, 2015, the substances of which are incorporated herein by reference.

FIELD OF INVENTION

This application relates to pessary devices for relief of female incontinence. More particularly, the present invention relates to pessary devices inserted with an applicator with improved ease having desirable expulsion characteristics

BACKGROUND OF THE INVENTION

Urinary incontinence, in which the ordinary bodily muscle functions fail to prevent unintended leakage of urine, is a common malady among women, particularly older women. It is estimated that up to 50% of women occasionally leak urine involuntarily, and that approximately 25% of women will seek medical advice at some point in order to deal with the problem. Stress incontinence, the most common type of urinary incontinence, refers to the involuntary loss of urine resulting from abdominal pressure rise, occurring during exercise, coughing, sneezing, laughing, etc. When stress incontinence occurs, it is usually the result of the abnormal descent of the urethra and bladder neck below the level of the pelvic floor. Many women wear sanitary napkins or diapers in order to deal with incontinence, and some women resort to surgical procedures.

Pessary devices are known to help relieve involuntary urination in a female. Such devices are designed for arrangement in the vagina for compressive action on and support of the bladder. Typical pessary devices are large in diameter during use, and can elastically expand, inflate, or unfold to provide compressive action within the vagina. Such pessary devices can be uncomfortable for a user and/or can require the user to activate or operate the device prior to or upon insertion of the pessary device into the vagina. This can result in an undesirable usage experience.

Further, the insertion process can pose additional obstacles. Some pessary devices require digital insertion into the body which may not be preferred. A preferred insertion method for many consumers is via an applicator. However, due to the size of the pessary needed to be effective and the desire to have minimal applicator sizes, the insertion process can create an undesirable usage experience. Some pessaries can also expand within an applicator increasing the force needed to expel the pessary upon insertion. Depending on the user's dexterity and hand strength, this can be problematic for many of the consumers wishing to use the product.

As such, there remains a need for a pessary device which can be more easily inserted via an applicator and deliver improved comfort.

SUMMARY OF THE INVENTION

An intravaginal pessary device housed within an applicator is disclosed. The device having an outer periphery defining a total area of the device and a central longitudinal axis, the applicator comprises a barrel region with a central longitudinal axis. The pessary device and the applicator exhibit a maximum expulsion force below 1,500 grams-force.

A non-expandable intravaginal pessary device having an outer periphery defining a total area of the device and an applicator having a barrel region enabled to house the pessary device is disclosed. The pessary device outer periphery has a maximum outer diameter, the applicator barrel region has an inner diameter, and the pessary device and applicator exhibit an expulsion force profile having a first peak below 5 Newtons.

An intravaginal pessary device having an outer periphery defining a total area of the device and an applicator having a barrel region enabled to house the pessary device is also disclosed. The pessary device and applicator exhibit an expulsion force profile having a first peak below 5 Newtons and have a maximum expulsion force of less than 1500 grams-force.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

The present invention is directed to pessary devices that are inserted into the female vagina with an applicator to help control involuntary urinary incontinence. The pessary devices can be non-expandable or expandable, small in size, easily insertable and can provide improved comfort during use. The pessary device's largest outer circumference can be smaller than the inner circumference of an applicator interior or of the same dimension.

The pessary devices can include a convex portion adapted to extend between an anterior vaginal wall and a posterior vaginal wall of a user to provide pressure on the user's urethra through the vaginal wall. The convex portion includes the maximum diameter of the pessary, wherein the maximum diameter is less than 35 mm. The pessary device also can include a second convex portion provided distal from the first convex portion. In addition, the pessary device also can include a region that can include the minimum diameter of the pessary device. The combined pessary device and applicator exhibit desirable expulsion characteristics including, but not limited to, expulsion force, force profile during expulsion, and work required to expel the pessary device from the applicator.

As used herein, "applicator" refers to a device or implement that facilitates the insertion of the pessary device into an external orifice of a mammal. Exemplary applicators include telescoping, tube and plunger, and compact applicators.

The term "joined" or "attached" as used herein, encompasses configurations in which a first element is directly secured to a second element by affixing the first element directly to the second element, configurations in which the first element is indirectly secured to the second element by affixing the first element to intermediate member(s) which in turn are affixed to the second element, and configurations in which first element is integral with second element, i.e., first element is essentially part of the second element.

As used herein, the term "non-expandable" refers to devices that do not expand prior to or during use, such as, for example, devices that do not increase in size or volume prior to or during use. For example, non-expandable devices have a diameter and/or volume that does not increase. In contrast, "expandable" as used herein, refers to devices that do increase in size or volume prior to or during use, such as, for example, devices that increase in diameter and/or length, absorb fluid into a fibrous or absorbent gelling material structure, or otherwise change from a first size or volume to a second size or volume, such as, for example, by inflation, absorption, mechanically, or by other means. Insubstantial changes to a non-expandable device as a result of any thermal expansion that could occur at body temperatures are not considered "expansion."

A "pessary device" or more particularly an "incontinence pessary device" as used herein refers to devices specifically designed, configured, and/or adapted for placement into a vagina in order to reduce the occurrence and/or severity of female urinary incontinence. A "pessary device" can include any type of substantially non-absorbent structure for the purpose of reducing urine leakage and/or supporting a prolapsed uterus and/or bladder. A pessary device does not include a menstrual tampon.

As used herein, the term "vaginal canal" refers to the internal genitalia of the human female in the pudendal region of the body. The terms "vaginal canal" or "within the vagina" as used herein are intended to refer to the space located between the introitus of the vagina (sometimes referred to as the sphincter of the vagina) and the cervix.

Figure 1A:
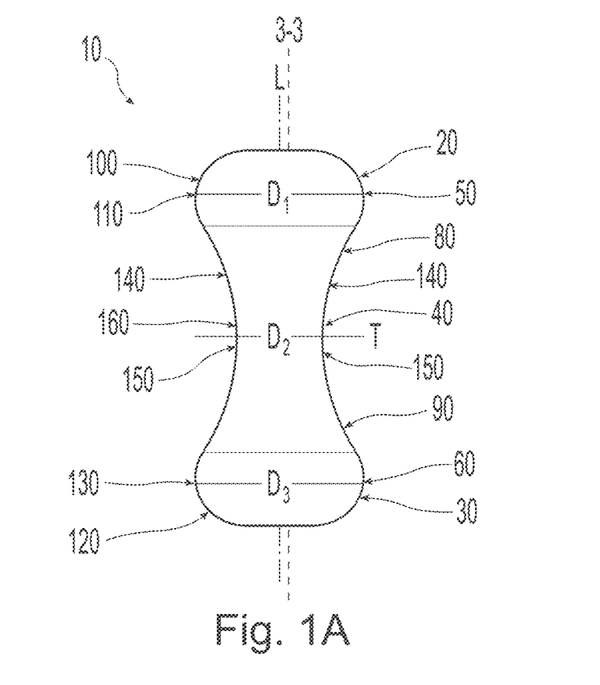
FIG. 1A is a side view of a pessary device.
Figure 1B:
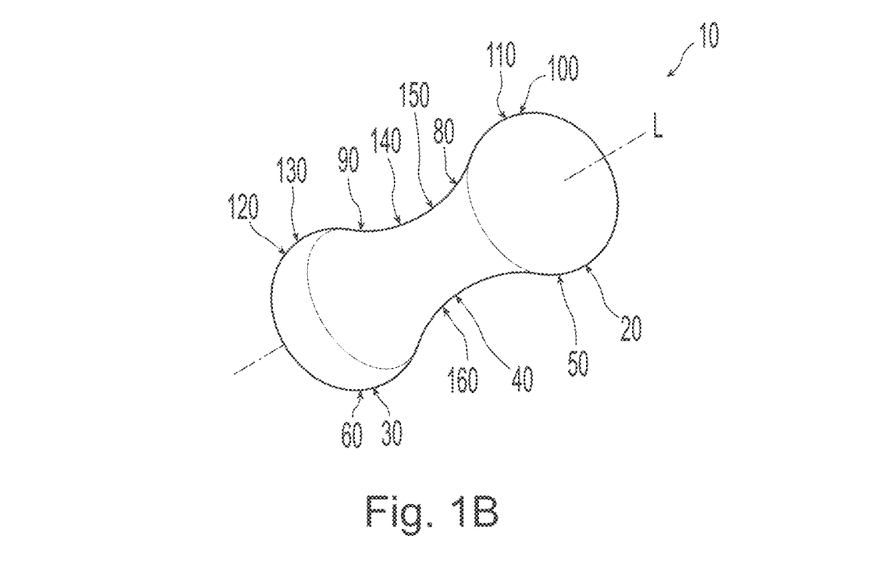
FIG. 1B is a perspective view of the pessary device of FIG. 1A.

An exemplary pessary device 10 is shown in FIGS. 1A and 1B. The pessary device 10 includes a top 20, a bottom 30, a mid-section 40, a convex portion 50 of the top 20, a convex portion 60 of the bottom 30, a maximum diameter D1, a minimum diameter D2, a sidewall 140 extending from the top 20 to the bottom 30, a longitudinal axis (L) and a transverse axis (T). As shown in FIGS. 1A and 1B, the pessary device 10 can have sidewalls 140 that include concave portions 150. The pessary device can be symmetric about the longitudinal axis, including for example, wherein the base is circular and symmetric about the longitudinal axis. The convex bottom portion 60 can have a maximum diameter D1 to provide convex portion 50. In addition, concave portion 150 can have a minimum diameter D2 that is less than maximum diameter D1.

Figure 2A:
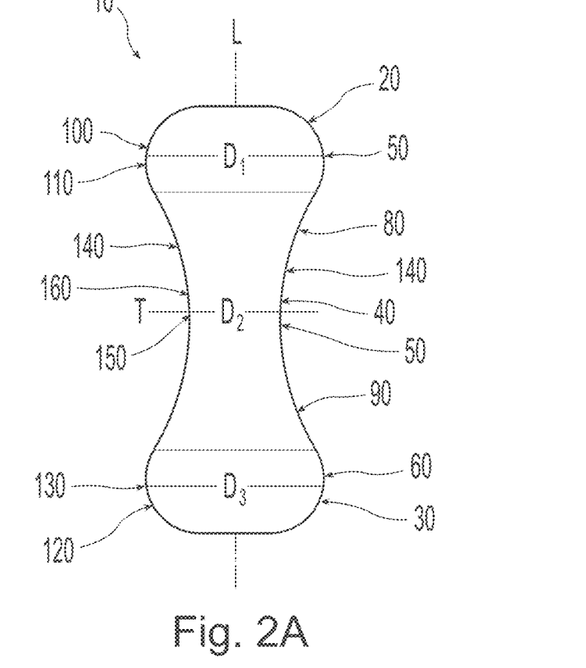
FIG. 2A is a side view of a pessary device.
Figure 2B:
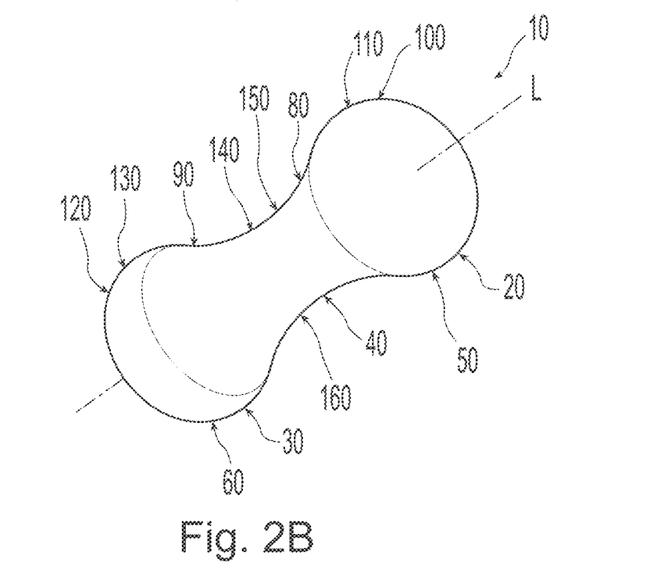
FIG. 2B is a perspective view of the pessary device of FIG. 2B.

FIGS. 2A and 2B show a pessary device 10. The pessary device 10 includes a top 20, a bottom 30, a mid-section 40, a convex portion 50 of the top 20, a convex portion 60 of the bottom 30, a maximum diameter D1, a minimum diameter D2, a sidewall 140 extending from the top 20 to the bottom 30, a longitudinal axis (L) and a transverse axis (T). As shown in FIGS. 2A and 2B, the pessary device 10 can have sidewalls 140 that include concave portions 150. The pessary device shown in FIGS. 2A and 2B has an upper slope 80 that is greater than the upper slope 80 of the pessary device shown in FIGS. 1A and 1B. In addition, the pessary device shown in FIGS. 2A and 2B has a lower slope 90 that is greater than the lower slope 90 of the pessary device shown in FIGS. 1A and 1B.

Figure 3:
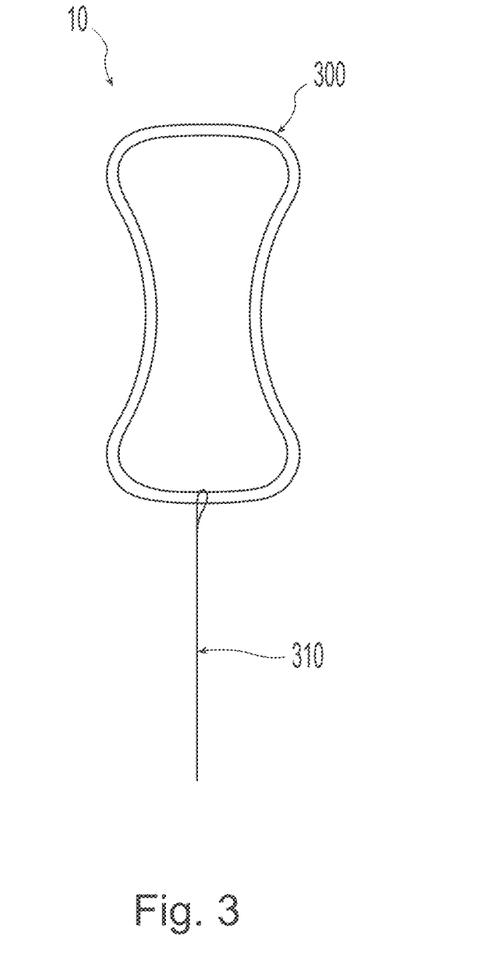
FIG. 3 is a side view of a pessary device.

The pessary device 10 can include an overwrap 300 and/or a withdrawal member 310, such as, for example, as shown in FIG. 3. In addition, FIG. 3 shows that withdrawal member 310 can be attached to overwrap 300.

Figure 4:
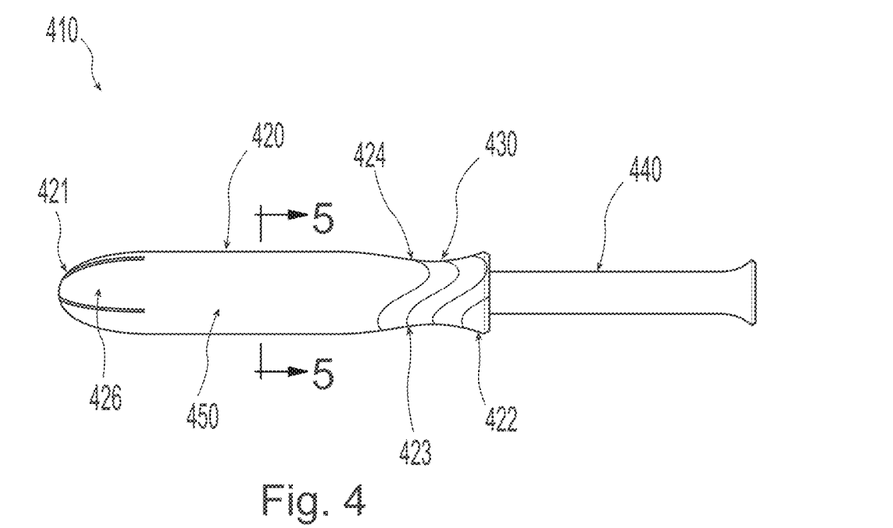
FIG. 4 is a side view of a pessary applicator, housing the pessary of FIG. 1.

The pessary device can be inserted using an applicator. FIG. 4 shows an applicator 410 that includes an insertion member 420 and a plunger 440. The insertion member 420 has an insertion end 421 and a withdrawal end 422 opposite the insertion end 421. The insertion member 420 also can include a barrel region 450 adapted to contain the pessary device, and a grip region 430 that can be an indentation region 424 provided opposite the insertion end 421, such as, e.g., proximal to the withdrawal end 422. The grip region 430 can include one or more grip elements 423.

The insertion end 421 can have one or more containing elements 426 to hold the pessary device within the applicator 410. A containing element can be in the form of a petal. A single petal can be used to hold the pessary device within the applicator until the user expels the pessary device. The insertion end can have between two and ten petals to hold the pessary device within the applicator until the user expels the pessary device.

The expulsion force necessitated to expel an intravaginal device from an applicator is equivalent to the sum of all the forces acting on the device. These forces can include the force needed to push through or open a petal design at an insertion end of an applicator, a force equal to the weight of the device to offset the gravitational force, and a frictional force arising from the normal force exerted by the device on the walls of an applicator. The amount of normal force can also depend upon whether the pessary device expands within the applicator thereby increasing the normal force or whether the normal force is created by the contact between the outer perimeter of the pessary device and the inner walls of the applicator.

Figure 5:
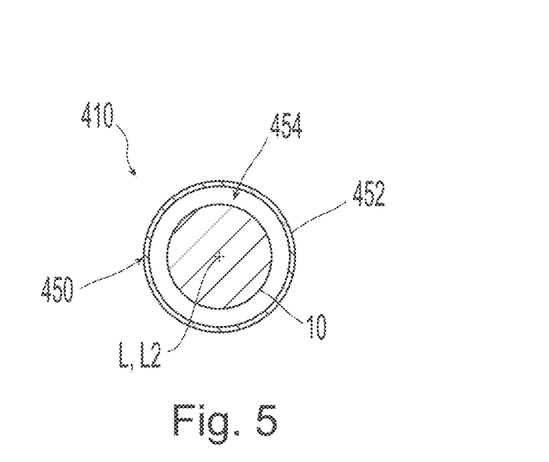
FIG. 5 is a cross section view of FIG. 4 taken along 5-5.

FIG. 5 shows a cross section of FIG. 4 taken along 5-5. The applicator 410 barrel region 450 has an inner surface 452. As shown in FIG. 5, a pessary device 10 is located within the applicator such that a gap 454 is formed between the pessary device 10 and the applicator inner surface 452 when the pessary device central longitudinal axis L is aligned with the applicator central longitudinal axis L2. As shown in FIG. 5, when the barrel region is circular, the gap 454 is annular.

It is understood that an overwrap as shown in FIG. 3 could add to the external surface of the overall pessary device. As shown in FIG. 5, the pessary device can create an annular gap without the overwrap. However, depending on the size of the device, the overwrap can be included as part of the pessary device while still having an annular gap between the applicator barrel region inner surface and the pessary device.

A non-expanding pessary device may not change in size during the usage experience, that is, the pessary device is the same size and diameter prior to insertion by the user as well as during use and removal. For example, the pessary device is not expandable or inflatable from its original size and the pessary device is not compressed for insertion into the user's body, nor is the pessary device compressed for withdrawal from the user's body. A portion or region of the pessary device can flex or be deformed, such as, for example, in the region having the minimum diameter, but the pessary device does not expand and returns to the original configuration after deformation. As such, the pessary device does not include any mechanical or other means that requires the user to change the size or shape of the pessary device during use, such as, for example, before or after insertion or prior to withdrawal. This provides for a pessary device that has a size upon withdrawal that is the same as the size during use, which can provide for improved comfort during use and withdrawal.

The pessary device can have a convex portion that has the maximum diameter of the pessary, such as, for example, at the base or at the top, that extends between the anterior vaginal wall and the posterior vaginal wall of a consumer to provide pressure on the urethra through the vaginal wall. In addition, the pessary device can have a second convex portion having an increased diameter as compared to the minimum diameter that can provide pressure on the urethra through the vaginal wall at a point distal from the first convex portion. The first convex portion and the second convex portion can be separated by any suitable distance, such as, for example, by at least about 5 mm, at least about 10 mm, at least about 15 mm, at least about 20 mm, at least about 25 mm, at least about 30 mm, at least about 35 mm, at least about 40 mm, at least about 45 mm, at least about 50 mm, or any other suitable distance.

The pessary device can have any suitable number of convex portions, including for example, four or fewer convex portions, three or fewer convex portions, two or fewer convex portions, one convex portion, or any other suitable number of convex portions.

The convex portion or portions can be any suitable shape, such as, for example, a convex shape that provides pressure to the vaginal wall, including, for example, a lobe or other protuberance. The convex portion or regions can have a substantially circular cross-section. The pessary device also can include a minimum diameter region that can provide flexibility to the pessary device, such as, for example, by allowing bending or movement at the minimum diameter region. The minimum diameter region can be any suitable shape, such as, for example, concave, indented, or the like, and can have any suitable cross-section, such as, for example, a substantially circular cross-section. The pessary device can include a concave region provided between two convex regions.

The pessary device can provide resistance to force when placed inside a woman's vagina. For example, when the pessary device is inserted into the vagina, increases in abdominal pressure can act as a force on the pessary device through the vaginal wall. When the pessary device is disposed in the vagina lengthwise, that is, with the top of the pessary device positioned toward the cervix, the bottom of the pessary device positioned toward the introitus, and the length of the pessary device generally aligned with the length of the vagina, increases in abdominal pressure can act on the side of the pessary device, perpendicular to the length of the pessary device. Of course, increases in abdominal pressure can act on other regions of the pessary device, in addition or alternatively to acting on the side of the pessary device, including for example, when the pessary device is inserted into the vagina in an orientation other than lengthwise.

Despite its small size, the pessary device can provide a resistance to force of greater than about 10 psi, greater than about 15 psi, greater than about 20 psi, or greater than about 25 psi under about 2 newtons of force. For example, the pessary device can provide a resistance to force of greater than about 20 psi under about 2 newtons of force and greater than about 25 psi under about 3 newtons of force. The pessary device also can resist compression under pressure. For example, the pessary device can compress less than about 20% under about 2 newtons of force, less than about 15% under about 2 newtons of force, less than about 14% under about 2 newtons of force, less than about 13% under about 2 newtons of force, less than about 12% under about 2 newtons of force, less than about 11% under about 2 newtons of force, less than about 10% under about 2 newtons of force, less than about 9% under about 2 newtons of force, less than about 8% under about 2 newtons of force, less than about 7% under about 2 newtons of force, less than about 6% under about 2 newtons of force, less than about 5% under about 2 newtons of force, less than about 4% under about 2 newtons of force, less than about 3% under about 2 newtons of force, less than about 2% under about 2 newtons of force, or less than about 1% under about 2 newtons of force.

The pessary devices can provide a varied resistance to force along the longitudinal axis of the pessary device. For example, the pessary device can provide a resistance to force that is greater at the maximum diameter regions and smaller at the minimum diameter regions. In addition, the pessary device can compress differently along the longitudinal axis at different regions. For example, when force is applied to the side of the pessary, the minimum diameter region can compress at least about 5% more than the maximum diameter region under the same amount of pressure (for example, under about 200 g/m2 of force), at least about 10% more than the maximum diameter region under the same amount of pressure, at least about 15% more than the maximum diameter region under the same amount of pressure, at least about 20% more than the maximum diameter region under the same amount of pressure, or at least 25% more than the maximum diameter region under the same amount of pressure. Any suitable amount of force can be applied, such as, for example, from about 200 g/m2 of force to about 1500 g/m2 of force, from about 200 g/m2 of force to about 1400 g/m2 of force, from about 300 g/m2 of force to about 1200 g/m2 of force, or from about 400 g/m2 of force to about 800 g/m2 of force.

The amount of resistance to force and the amount of compression under force provided by the pessary device as a whole or provided by the different regions of the pessary device can be measured in any suitable manner. For example, one suitable method employs a Universal Constant Rate Elongation/Tensile Tester with computer interface (MTS, Eden Prairie, Minn.). The method measures the force required to compress the pessary device resting on its side at 0.8 mm at a rate of 20 mm per min. For this method, the load probe tip is 5 mm in diameter and the tip is semi-spherical in shape. In addition, the resting fixture is a cylindrical steel plate 152 mm in diameter and 13 mm thick. The pessary device is placed on the steel table and the crosshead moves at 20 mm/min. When a force of 2 grams is exhibited on the pessary device, the crosshead automatically zeroes out and moves an additional 0.8 mm. The probe cycles back, and data is acquired at a rate of 100 Hz. This method measures the peak force in grams versus the amount of compression in mm. For pessary devices having varying diameters or widths, such as, for example, pessary devices having a maximum diameter or width and a minimum diameter or width, resistance to force at the different regions can be measured using this method. For example, for a pessary device as shown in FIGS. 1A and 1B, resistance to force at the maximum diameter regions D1 and D3 can be measured using a steel plate that is larger in size than the pessary device as the resting fixture. Resistance to force at the minimum diameter region D2 can be measured using a single rod that contacts the minimum diameter region but not the maximum diameter regions.

Generally, the convex portion can be resistant such that the convex portion can provide pressure to the vaginal wall. The convex portion can provide resistance under high stress pressures typical of the human vagina, such as, for example, by providing a maximum pressure to the urethra through the vaginal wall greater than about 5 psi, such as, for example, greater than about 10 psi, greater than about 15 psi, greater than about 20 psi, or greater than about 25 psi. In addition, the pressure region can provide a maximum urethral closure of greater than about 1.0 mm, such as, for example, greater than about 1.1 mm, greater than about 1.2 mm, greater than about 1.3 mm, greater than about 1.4 mm, such as, for example, greater than about 1.5 mm, greater than about 1.6 mm, greater than about 1.7 mm, greater than about 1.8 mm, or greater than about 1.9 mm. In addition, or alternatively, the convex portion can compress less than about 1 mm when measured under 0.5 psi when the force is applied from one side of the convex portion to the opposite side of the convex portion at the region of maximum diameter in the direction perpendicular to the longitudinal axis.

Maximum pressure to the urethra and maximum urethral closure can be measured using any suitable method, such as, for example, by using the computational model described in U.S. Patent Appln. No. 2007/0027667. For example, a computation model simulating the human internal pelvic environment can be used. In certain embodiments, thirteen nodes on the urethra in the simulation that are both on the back wall toward the vagina and in the middle of the body on the sagittal plane can be chosen. The points should be spread even along the length of the urethra with the first point at the bottom edge of the urethra and the last point at the bladder neck. Node vs. time vs. Von Mises stress should be obtained using a suitable software program, such as, for example, LS-Prepost, for all chosen nodes. The data columns are then matched to determine the y position vs. time vs. Von Mises stress. Generally, only the data that is at the simulation end point should be selected and y-position vs. Von Mises is then plotted.

The minimum diameter region, on the other hand, can be more flexible than and provides less resistance than the convex portion. Addition of the minimum diameter region can allow the pessary device to flex in the longitudinal direction as well at the lateral direction. For example, the pessary device can compress more than about 1 cm when measured under 0.5 psi when the force is applied from the top to the base along the longitudinal axis. In addition, or alternatively, the minimum diameter region can provide a bending region that facilitates the pessary device bending from side to side.

The pessary device can be a unitary construction. For example, the pessary device can include a continuous outer shell that defines the entire exterior surface of the pessary device. The outer shell can be smooth or textured. The outer shell can be permeable to fluid, such as, for example, by the inclusion of holes, pores, or other suitable openings. Alternatively, the outer shell can be impermeable to fluid such that fluid cannot enter the device. In addition, the pessary device can include an opening in the top and/or base. The pessary device can include an opening in the top and/or base and the outer shell is not permeable to fluid such that fluid cannot enter the device except through the opening in the top and/or base.

Suitable pessary devices can be solid or can have a hollow interior. For hollow devices, the pessary device can have an outer periphery defining a total area of the device and an inner periphery defining an open area of the device. The open area can be any suitable size, such as, for example, between about 5% to about 95% of the total area, such as, for example, from about 10% to about 90% of the total area, from about 15% to about 85% of the total area, or from about 20% to about 80% of the total area. In addition, the pessary device also can have a wall thickness that is suitable to maintain the pessary configuration. The wall thickness can be greater than about 1 mm, such as for example, about 2 mm, about 3 mm, about 4 mm, about 5 mm, or greater. The wall thickness can be constant or varied along the length of the pessary device and/or around the circumference of the pessary device.

Figure 8:
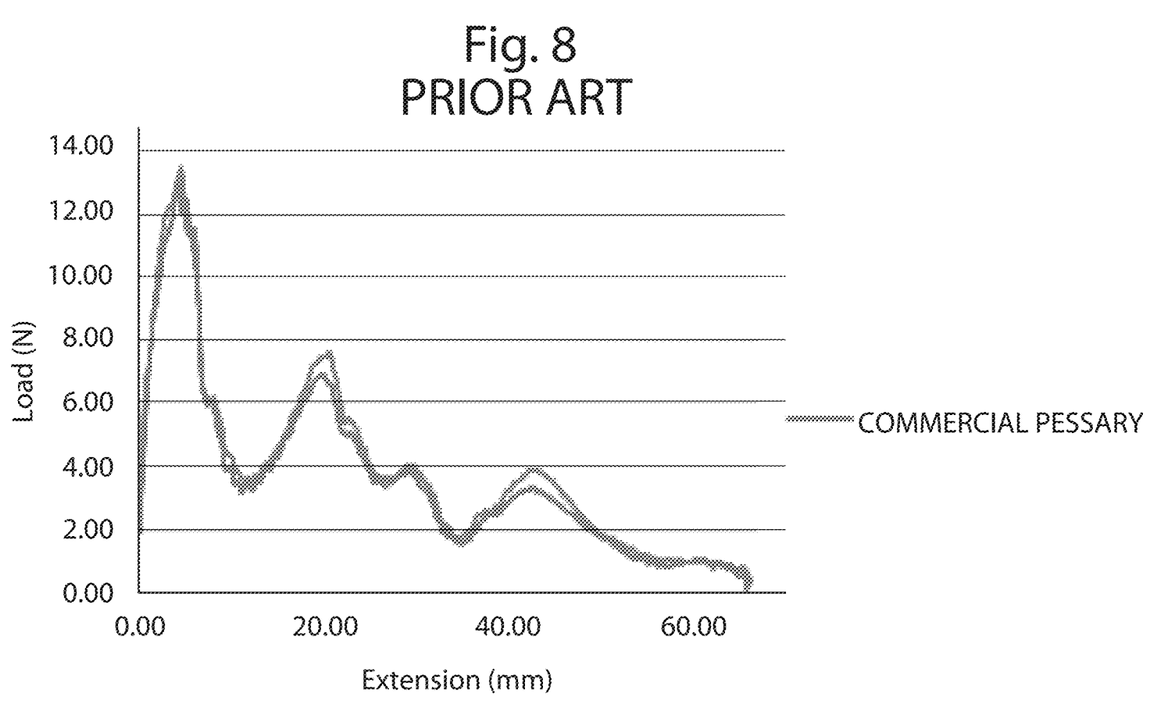
FIG. 8 graphs the force profile to expel a commercial pessary from its applicator.

The pessary device can have any suitable shape having a varied diameter along the longitudinal axis, such as, for example, a shape having a varied diameter that is symmetrical with respect to the longitudinal axis, such as, for example, a teardrop, an apple, a pear, an hourglass, a waisted cylinder, a figure-8 shape, a peanut shape, a heart-shape, a light bulb shape, a bottle shape, a vase shape, or any other suitable shape. In addition, the shape can have a varied diameter and can be symmetrical with respect to both the longitudinal and lateral axis, such as, for example, an hourglass, a waisted cylinder, a figure-8 shape, a peanut shape, or any other suitable shape. Alternatively, the pessary device can have an asymmetrical shape, such as, for example, a B-shape or a P-shape. The pessary device can be symmetrical at one region and asymmetrical at another region, such as, for example, where the pessary device has a symmetrical pressure region and an asymmetrical flexile region. Generally, the pessary device can have a varying diameter that can provide varying pressure along the user's urethra. For example, the pessary device can have a maximum diameter region that can correspond to the convex portion. In addition, the pessary device can have a minimum diameter region that can be a concave region.

The pessary device can be hourglass shaped. For example, as shown in FIGS. 1-2, the pessary device can have upper and lower portions joined together by a waistline portion, with the upper and lower portions having diameters that are both greater than a diameter of the waistline portion such that the pessary device has a generally hourglass configuration. In this configuration, the upper portion of the pessary device can have a top and the lower portion of the pessary device can have a base, and the pessary device can have sloping upper and lower wall sections joining the top and the base with the waistline portion. In addition, the waistline portion can include the minimum diameter of the pessary device. The upper and lower portions can have generally coequal maximum diameters, or the upper and lower portions can have different maximum diameters, such as, for example, where the upper portion has a maximum diameter greater than the lower portion or where the lower portion has a maximum diameter greater than the upper portion.

Generally, the pessary device includes at least one maximum diameter and at least one minimum diameter, where the minimum diameter is smaller than the maximum diameter. The pessary device can include a first portion having a maximum diameter, a second portion having a maximum diameter, and a third portion that has a minimum diameter. The maximum diameter of the first portion and the maximum diameter of the second portion can be separated by a distance that is greater than about 10% of the length of the pessary device, such as, for example, by a distance greater than about 5 mm, greater than about 10 mm, greater than about 15 mm, greater than about 20 mm, greater than about 25 mm, greater than about 30 mm, greater than about 35 mm, greater than about 40 mm, greater than about 45 mm, or more. The pessary device can provide pressure at mid-urethra, the bladder neck, or both. In addition, the pessary device can provide higher pressure at the mid-urethra, the bladder neck, or both and provides lower pressure at the area between the mid-urethra and the bladder neck. For example, the pressure region can provide pressure at levels about 25% higher than the pressure provided by the flexile region, such as, for example, at levels about 30% higher, about 35% higher, about 40% higher, about 45% higher, about 50% higher, about 55% higher, about 60% higher, or more.

The pessary device can have a slope from the maximum diameter to the minimum diameter. Any suitable slope can be used, including for example, about 0.25 mm, about 0.5 mm, about 0.75 mm, about 1 mm, about 1.5 mm, about 2 mm, about 2.5 mm, about 3 mm, about 4 mm, about 5 mm, about 6 mm, about 7 mm, about 8 mm, or more, such as, for example, a slope from about 0.25 mm to about 5 mm, or a slope from about 0.5 mm to about 4 mm, or any other suitable range.
The slope of the pessary device from the minimum diameter to the maximum diameter needs to be considered when combining with an applicator for expulsion. If the shape of the transition deviates too far from the angle of the petals at the insertion end, a force spike may result which can hinder the insertion process. The slope of the transition should therefore not deviate from the slope of the petal by more than 40%, such as between 0% and 40%, such as for example, 5%, 10%, 15%, 20%, 25%, 30%, or 35%.

Suitable pessary devices are typically smaller in size than conventional pessary devices. For example, the pessary devices have a maximum diameter, a length, and/or a volume that is smaller or less than that of conventional pessary devices.

The pessary devices can have any suitable maximum diameter, such as, for example, a maximum diameter of less than 35 mm, such as, for example, less than 34 mm, less than 33 mm, less than 32 mm, less than 31 mm, less than 30 mm, less than 29 mm, less than 28 mm, less than 27 mm, less than 26 mm, less than 25 mm, less than 24 mm, less than 23 mm, less than 22 mm, less than 21 mm, less than 20 mm, less than 19 mm, less than 18 mm, less than 17 mm, less than 16 mm, less than 15 mm, less than 14 mm, less than 13 mm, less than 12 mm, less than 11 mm, or less than 10 mm, including, for example, a maximum diameter of from about 10 mm to about 35 mm, from about 10 mm to about 25 mm, from about 13 mm to about 25 mm, or from about 15 mm to about 22 mm. The maximum diameter or width is typically measured at the widest portion of the pessary device substantially perpendicular to the longitudinal axis.

The pessary devices can have any suitable minimum diameter that is smaller than the maximum diameter, including, for example, a minimum diameter from about 40% to about 95% of the maximum diameter, from about 40% to about 90% of the maximum diameter, from about 40% to about 85% of the maximum diameter, from about 40% to about 80% of the maximum diameter, from about 45% to about 75% of the maximum diameter, or from about 50% to about 70% of the maximum diameter, such as, for example, about 45% of the maximum diameter, about 50% of the maximum diameter, about 55% of the maximum diameter, about 60% of the maximum diameter, about 65% of the maximum diameter, or about 70% of the maximum diameter.

The pessary devices can have a minimum diameter from about 4 mm to about 28 mm, about 5 mm to about 20 mm, about 8 mm to about 20 mm, from about 8 mm to about 18 mm, or from about 8 mm to about 15 mm, such as, for example, about 8 mm, about 8.5 mm, about 9 mm, about 9.5 mm, about 10 mm, about 10.5 mm, about 11 mm, about 11.5 mm, about 12 mm, about 12.5 mm, about 13 mm, about 13.5 mm, about 14 mm, about 14.5 mm, about 15 mm, about 15.5 mm, about 16 mm, about 16.5 mm, about 17 mm, about 17.5 mm, about 18 mm, about 18.5 mm, about 19 mm, about 19.5 mm, or about 20 mm, or any other suitable minimum diameter. The minimum diameter or width is typically measured at the narrowest portion of the pessary device substantially perpendicular to the longitudinal axis.

The maximum diameter and the minimum diameter can be separated by any suitable distance, such as, for example, by about 5 mm, about 10 mm, about 15 mm, about 20 mm, about 25 mm, about 30 mm, about 35 mm, about 40 mm, about 45 mm, about 50 mm, or any other suitable distance.

The pessary devices can have any suitable length, such as, for example, a length from about 35 mm to about 60 mm, about 40 mm to about 55 mm, or about 40 mm to about 50 mm, such as, for example, a length about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, or about 50 mm. The length is typically measured substantially parallel to the longitudinal axis of the pessary device.

Generally, the pessary device can have a weight of less than about 10 grams, less than about 9 grams, less than about 8 grams, less than about 7 grams, less than about 6 grams, less than about 5 grams, less than about 4 grams, less than about 3 grams, less than about 2 grams, or about 1 gram, including for example, a weight of from about 1 gram to about 7 grams, or from about 2 grams to about 6 grams, or from about 1 grams to about 4 grams, or from about 3 grams to 5 grams Pessary devices can be fabricated using any suitable materials and methods. For example, pessaries can be formed from polymeric materials, such as, for example, polycarbonate, polyester, polyethylene, polyacrylamide, polyformaldehyde, polymethylmethacrylate, polypropylene, polytetrafluoroethylene, polytrifluorochlorethylene, polyvinylchloride, polyurethane, nylon, silicone, or mixtures or blends thereof, or metallic materials. In certain embodiments, the pessary devices are not formed from absorbent material such as, for example, fibrous material or absorbent foam.

Pessary devices can be formed in any suitable manner, such as, for example, using injection molding or other suitable methods of forming the pessary device.

The pessary device can be covered by an overwrap. The overwrap can be non-absorbent or absorbent and can include any suitable material, such as, for example, a fibrous nonwoven material comprising natural, synthetic, or a blend of natural and synthetic fibers. Suitable synthetic fibers can include, e.g., fibers such as polyester, polyolefin, nylon, polypropylene, polyethylene, polyacrylic, cellulose acetate, polyhydroxyalkanoates, aliphatic ester polycondensates, bicomponent fibers and/or mixtures thereof. Natural fibers can include, e.g., rayon and those commonly known to be non-synthetic and of natural origin such as cotton. The fibers can have any suitable cross-sectional shape, such as, e.g., round, tri-lobal, multi-lobal, delta, hollow, ribbon-shaped, and/or any other suitable shape, or mixtures thereof. Fibers with any suitable diameter can be used, such as, e.g., from about 0.5 to about 50 microns, such as, e.g., from about 1 to about 30 microns, such as, e.g., from about 10 to about 25 microns. Fiber diameter can be determined using any suitable means; however, for non-round fibers, diameter can typically be determined by reference to the diameter of a fiber with the same cross-sectional area as the non-round fiber.

The overwrap can be made by any number of suitable techniques and can have any suitable basis weight. Suitable techniques include, for example, carding, meltblowing, spunbonding, spunlacing, air laying, and the like. For example, the overwrap can be formed using bonding methods, such as, e.g., thermal, ultrasonic, resin, through-air bonding, hydroentangling, and/or needling. The basis weight of the overwrap can be any suitable weight, such as, e.g., from about 10 to about 60 grams per square meter (gsm), such as, e.g., from about 15 to about 30 gsm. In addition, the overwrap can be hydrophilic or hydrophobic.

The overwrap can be joined to the pessary device by any variety of means. The overwrap can be joined to itself or to the pessary device. For example, one portion of overwrap can be joined to an opposed portion of the overwrap or to the pessary device using any suitable adhesive or heat pressure bonding means. Such adhesive can extend continuously along the length of attachment or it can be applied in a non-continuous fashion at discrete intervals. Heat bonding includes thermally bonding, fusion bonding, or any other suitable means for joining such materials.

Pessary devices can also include lubricants applied to the overwrap material to reduce the frictional force within the applicator upon insertion. These ingredients serve to reduce the coefficient of friction thereby lowering the frictional force when the normal force of the pessary device acting on the applicator walls cannot be reduced enough. Lubricants may be water based or oil based. Some examples may include glycerin, mineral oil, petroleum jelly, silicone or water.

The pessary device can include a withdrawal member that can comprise any suitable material, including for example, cotton, cellulose, rayon, polyolefins such as, for example, polyethylene or polypropylene, nylon, silk, polytetrafluoroethylene, wax, or any other suitable materials.

The withdrawal member can be formed by any suitable formation method and in any suitable configuration, such as, e.g., one or more cords, strings, finger covers, ribbons, an extension of a material of the device, or combinations thereof.

The pessary device is inserted using an applicator that can include an insertion member and a plunger. The insertion member can have an insertion end and a withdrawal end opposite the insertion end. The insertion member also can include a barrel region adapted to contain the pessary device, and a grip region that can be an indentation region provided opposite the insertion end, such as, e.g., proximal to the withdrawal end.

The barrel region diameter can be larger than the largest pessary diameter such that a gap is created between the barrel region inner surface and the pessary device outer surface when the pessary device is aligned along the central longitudinal axis of the applicator barrel region. When the barrel region is in the form of a circle, the gap is annular. When the barrel region is in a shape that is not circular, the gap can take the shape of the inner surface of the barrel region such that, when the applicator and the pessary device share a common central longitudinal axis, the pessary device outer surface does not contact the barrel region inner surface. The annular gap can be, for example, 0.01 mm to 3 mm, 0.1 mm to 2 mm, 0.5 mm to 1 mm, such as for example 0.2 mm, 0.3 mm, 0.4 mm, 0.5 mm, 0.6 mm, 0.7 mm, 0.8 mm, 0.9 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm.

The relationship between the outer circumference of the pessary device and the inner circumference of the applicator barrel region can comprise a ratio of between 0.3:1 to 0.99:1, such as, for example, 0.35:1, 0.4:1, 0.45:1, 0.5:1, 0.55:1, 0.6:1, 0.65:1, 0.7:1, 0.75:1, 0.8:1, 0.85:1, 0.9:1, 0.91:1, 0.92:1, 0.93:1, 0.94:1, 0.95:1, 0.96:1, 0.97:1, or 0.98:1.

The combination of the applicator and the pessary device has a maximum expulsion force of less than 2000 grams-force, such as, for example, between 0 and 1,500 grams-force, between 100 grams-force and 1,000 grams-force, between 200 grams-force and 800 grams-force, between 300 grams-force and 750 grams-force, between 350 grams-force and 600 grams-force, between 400 grams-force and 500 grams-force.

It has been found that the expulsion force needed to insert the pessary device is actually the sum of a frictional force created by the pessary device contacting the inner surface of the applicator barrel region, the force needed to offset the weight of the pessary device due to gravity, and the force needed to open the petals or potential restriction that maintains the pessary device in the applicator.

Creating a desirable usage experience during insertion represents reducing the expulsion force to increase the ease of insertion. A large component of the expulsion force is frictional force. Applicants have found that the normal force can be reduced or made negligible by creating a gap between the applicator barrel region and the pessary device, thereby lowering the frictional force. The annular gap is formed by a barrel region diameter that is larger than the largest diameter of the non-expandable pessary device. Further, by minimizing the normal force, it has been surprisingly found that one can utilize thin walls for the applicator. This is unlike an applicator that is used with an expanding pessary device which may require walls thick enough to withstand any pressures exerted by the expanding device.

TABLE 1

Maximum Expulsion Force Using Tensile Tester
for Pessary Devices using Applicators

| Product | Average Maximum Expulsion Force (g) |
|---|---|
| Commercial Pessary 1 | 1352 |
| Commercial Pessary 2 | 1387 |
| Invention A | 285 |
| Tampax Ultra | 293 |

It has also been found that, by using a lightweight pessary device, one can offset the normal force and force of gravity to create combined applicator and pessary device with an expulsion force that is in line with light weight tampons instead of traditional pessary devices. In general, the maximum expulsion force for tampons typically range from 200 grams-force to 800 grams-force. The maximum expulsion force is a measure of the highest force needed in the process of expelling a device from the applicator.

The proposed combined pessary device and applicator requires less work to expel the pessary device from the applicator. As shown in Table 2 below, the work required to expel the pessary device can be less than the work required to expel a tampon.

| Product | Average Work to Expel Device (N * mm) |
|---|---|
| Invention A | 925 |
| Tampax Ultra | 1105 |
| Commercial Pessary 1 | 2177 |
| Commercial Pessary 2 | 2111 |

Figure 6:
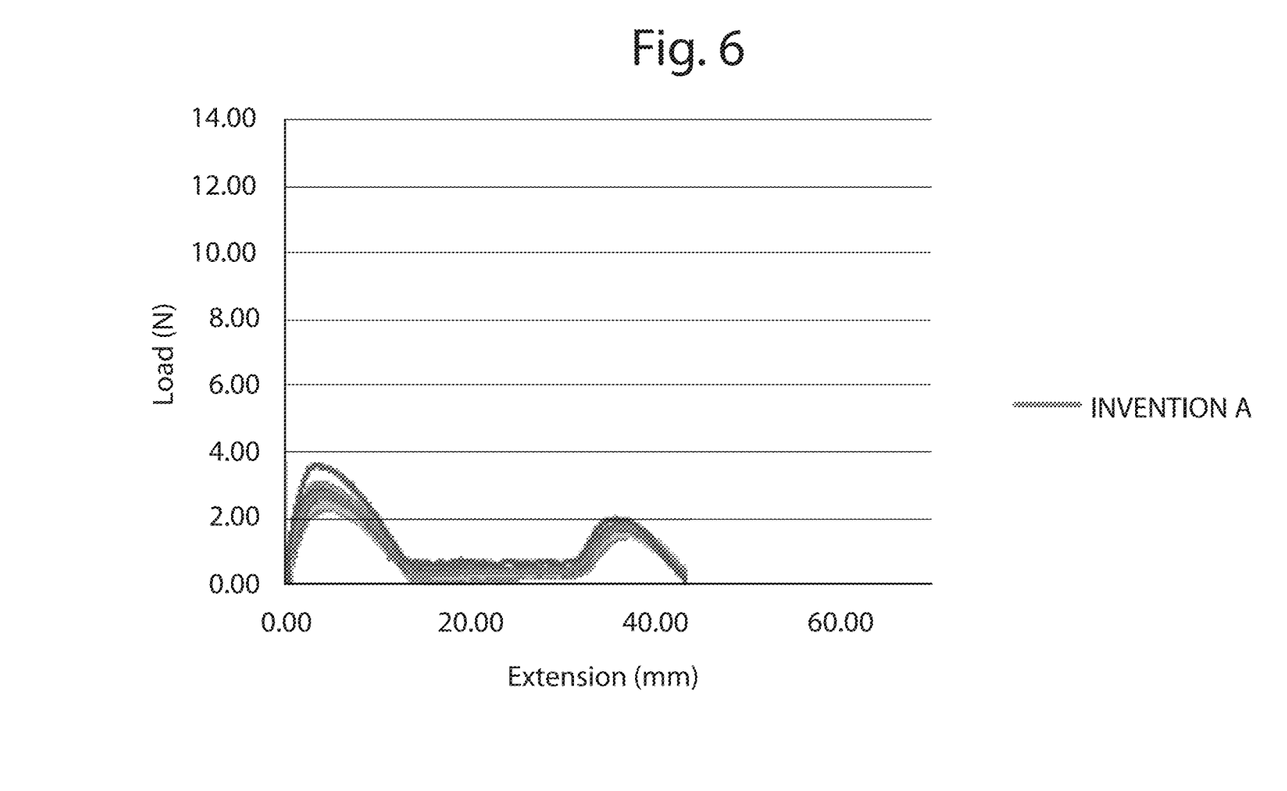
FIG. 6 graphs the force profile to expel the claimed pessary device from its applicator.
Figure 7:
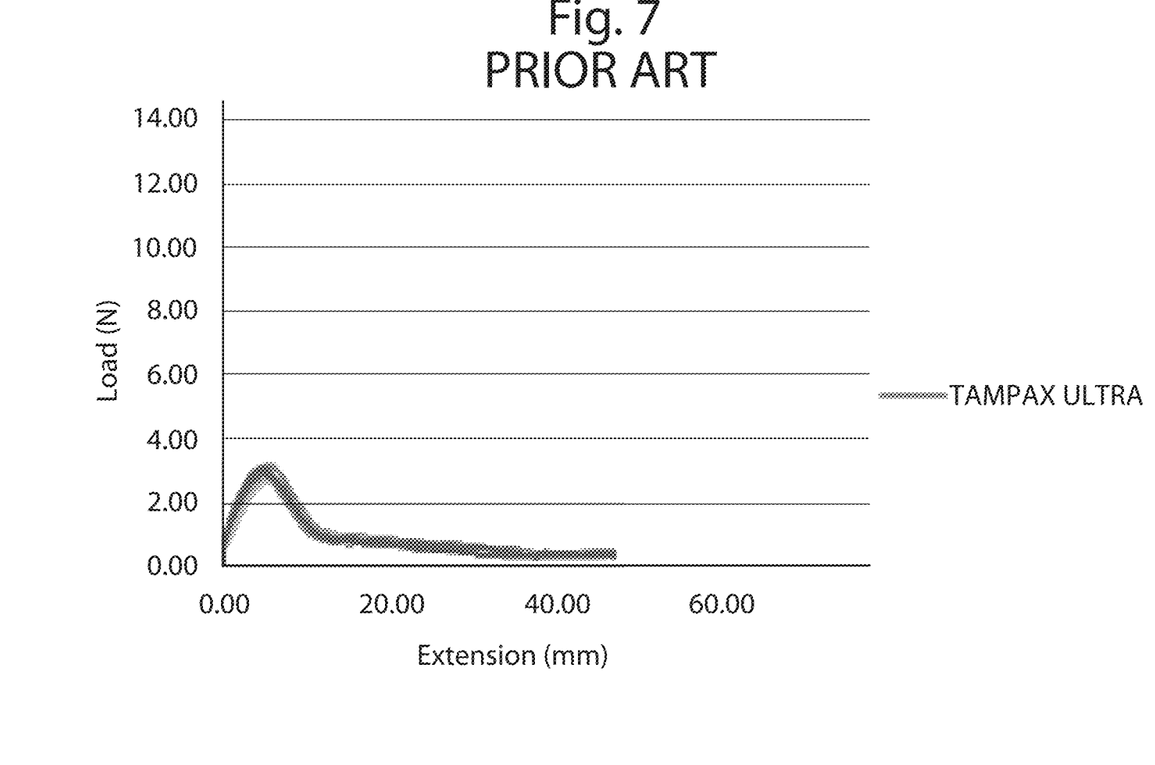
FIG. 7 graphs the force profile to expel a Tampax Ultra from its applicator.

As shown in FIGS. 6-8, the expulsion force profile of Invention A (FIG. 6) has a two peak structure wherein neither peak exceeds 4 newtons, the second peak is a percentage of the first peak, and the area between the two peaks drops to nearly zero newtons. Comparing the expulsion force profile of FIG. 6 to that of a tampon (FIG. 7), it is noted that both have a similar max peak force of less than 5 newtons. However, unlike the tampon expulsion force profile which gradually decreases after the initial peak, Invention A has an expulsion force profile that drops to nearly zero for a large portion of the device. This allows Invention A to have a lower total work requirement versus the tampon.

As shown in FIG. 8, the commercial pessary expulsion force profile has multiple peaks. The first peak and the second peak both exceed 5 N. In addition to the two first peaks, there are two more inflection points in the slope of the force profile where the force required increases creating a four peak profile wherein at least the first two peaks are above 5 newtons. In comparison to both the tampon and Invention A, the commercial pessary is both harder to expel, requiring more force as one moves through the expulsion process, and more overall work to expel the device as seen in Table 2.

The insertion member and/or plunger can be constructed from any suitable material. Suitable materials include, for example, paper, paperboard, cardboard, cellulose, such as, e.g., molded cellulose, or any combinations thereof, polyethylene, polypropylene, polybutylene, polystyrene, polyvinylchloride, polyacrylate, polymethacrylate, polyacrylonitrile, polyacrylamide, polyamide, nylon, polyimide, polyester, polycarbonate, polylactic acid, poly hydroxyalkanoate, ethylene vinyl acetate, polyurethane, silicone, derivatives thereof, copolymers thereof, mixtures thereof, or any suitable smooth plastic material. Examples of suitable materials are disclosed in, e.g., U.S. Pat. Nos. 5,346,468 and 5,558,631. Additives can be included in the material to alter or enhance certain material properties. Suitable additives include, for example, mold release agents, slip agents, surface energy modifiers, pearlescent agents, and/or any other suitable additives. The insertion member also or alternatively can be coated with a substance to give it a high slip characteristic, such as, e.g., with wax, polyethylene, a combination of wax and polyethylene, cellophane, clay, mica, and other lubricants that can facilitate comfortable insertion. Alternatively, or in addition, the insertion member can include a textured surface. Texture can be provided in any suitable manner, such as, e.g., by designing texture into or adding texture to the insertion member.

The applicator walls can be between 0.1 mm and 2 mm, such as, for example, 0.2 mm, 0.3 mm, 0.4 mm, 0.5 mm, 0.6 mm, 0.7 mm, 0.8 mm, 0.9 mm, or 1.0 mm.

The barrel portion of the applicator can be sized and configured to house a feminine hygiene product, such as, e.g., an absorbent tampon and/or pessary. The size of the barrel portion can be determined primarily by the dimensions of the feminine hygiene product. For example, the barrel portion can have inner diameters of about 5.0 millimeters to about 22.0 millimeters and a wall thickness of about 0.1 millimeter to about 2.0 millimeters. The inner diameter of the barrel portion can be greater than the diameter of the feminine hygiene product to prevent the barrel portion from interfering with the expulsion of the feminine hygiene product from the barrel portion. The inner diameter of the barrel portion can have varying diameters and shapes to conform to the profiled shape of the enclosed feminine hygiene product, such as, e.g., a pessary. The barrel portion can have a length sufficient to house the feminine hygiene product prior to the expulsion of the feminine hygiene product from the applicator into the vagina.

The barrel portion can be of any suitable cross-sectional shape. The barrel portion can include a generally non-circular cross-sectional shape, such as, e.g., oval, rectangular, elliptical, oblate, or other suitable shapes. The barrel portion can have a cross-sectional shape that has a greater thickness than width or vice versa. The barrel portion can have a substantially uniform cross-section, such as, e.g., having the same cross-section along the length. The barrel portion can have varying cross-sectional shapes and/or cross-sectional sizes, such as, e.g., a barrel portion having a smaller cross-sectional area near the insertion end of the barrel and a larger cross-sectional area near the opposite end.

The insertion end of the barrel portion can be open-end or closed-ended. The insertion end of the barrel portion can include petals, corrugations, pleats, a film cap, or other means for covering the barrel portion prior to expulsion of the tampon. In certain embodiments, the material, such as, e.g., a feminine care product can be loaded into the barrel portion prior to covering the insertion end of the barrel portion. Alternatively, the insertion end of the barrel portion can be covered prior to loading the feminine hygiene product into the barrel portion.

The insertion end can have at least one containing element. The containing element maintains the pessary device within the applicator until it is expelled by a user. The containing element can be, for example, a petal, a plurality of petals, a strip of material that obstructs the barrel region insertion end, and a cap attached to the barrel region. The containing element can be integral to the applicator or attached to the applicator. The containing element can be made from a different material than the applicator such as, for example, a film. The film can be made of one or more of the following substrates and resins: polyolefins, cellulose materials and derivatives, including cellulose ethers, ethyl and/or methyl celluloses, cellulose esters, including cellulose acetates, and/or formates, vinyl polymer derivatives, or more typically cellophane and/or polyethylenes, polypropylenes, PET, PVC, latex, nylon, polyesters, polystyrenes. Some other resins and films include polylactides, polyester amides, aliphatic esters, aliphatic-aromatic copolyesters, polyhydroxyalkonoates, polvalkulene succinate, polyvinyl alcohols, cellulosic polymers, starch-based materials and/or polycaprolactone. Polyolefin, such as polyethylenes and polypropylenes and/or biodegradable films are typical.

The containing element can be a film cap as disclosed in U.S. Pat. No. 6,958,057. The film cap can be made of any type of planar, flexible film or other deformable substrate. The typical film material used to make a film cap can be a sheet-shaped substrate that can smooth or embossed. Some materials include paper, woven and non-woven substrates, cloths, metal foils, cellulose fiber sheets, and organic polymeric materials.

The insertion member can include a grip region, such as, for example, an indentation region. The grip region can have a plurality of three-dimensional surface elements, such as, e.g., projections, rings, ridges, ribs, embossments, depressions, grooves, and/or other gripping structures. The three-dimensional surface elements can be provided in any suitable manner, such as, e.g., by the addition of material, and/or by impressing, such as, e.g., by embossing, or compressing the surfaces. For example, the indentation region can include one or more flattened sides and/or one or more spaces for a decorative marking or a character, such as, e.g., an embossed and/or printed marking or character. In addition, or alternatively, the surfaces of the indentation region can include a material that can provide a frictional resistance for the user's fingers during the insertion of the applicator into the body. Suitable materials that can provide friction include, for example, abrasive materials, high wet coefficient of friction materials, pressure sensitive adhesives, or any combinations thereof.

The gripping indicia can communicate to a user where the grip portion is located on the applicator, which can assist the user in proper placement of her fingers on the grip portion and/or can increase the user's confidence in proper handling of the applicator. In addition, or alternatively, the gripping indicia can communicate to a user the identity and/or absorbency of material disposed within the applicator, can indicate to a user when the applicator is fully inserted, and/or can increase user enjoyment. The gripping indicia can show a user how to properly orient an applicator, such as, e.g., an applicator having a non-circular cross-sectional shape and/or an applicator containing material with more expansion in a direction, such as, e.g., width-wise expansion.

The visual indicia can also be a pattern, such as, e.g., a printed, molded, adhered, hot stamped, screen printed, pressure sensitive label, therimage label, shrink sleeve, and/or painted pattern. The visual indicia can be a line or can provide the perception of a line, such as, e.g., a colored line, a patterned line, a broken line, or a foil line, that can be positioned to provide a gripping indicia, such as, e.g., to demarcate the grip portion from the barrel portion and/or the plunger portion.

The gripping indicia can be tactile indicia. Any tactile indicia suitable from distinguishing the grip portion from the barrel portion and/or the plunger can be used, such as, e.g., textures, embossments, raised printing, compressible material, such as, e.g., rubber, silicone, and/or foam, and/or other material that can increase the coefficient of friction of the grip portion. The tactile indicia can be a generally uniform texture, such as, e.g., a coating or additive applied to the grip portion, as compared to a generally discontinuous texture, such as, e.g., a series of ribs, ridges, or raised portions. Tactile indicia can, for example, distinguish the grip portion from the barrel portion and/or the plunger and/or can provide the user with improved applicator control and decreased finger slippage.

The gripping indicia can be made in any suitable manner, such as, e.g., by printing, stamping, embossing, injection molding, reforming, such as, e.g., via heat, dipping, such as, e.g., in a liquid solution, co-injection molding, taping, adhering, painting, screen printing, pressure sensitive labeling, hot stamping, therimage labeling, shrink sleeve, dimensional coating, combinations thereof, and/or any other suitable manner.

The grip portion can be constructed from any suitable material. The barrel portion can be constructed from any suitable material. Suitable materials include, for example, paper, paperboard, cardboard, cellulose, such as, e.g., molded cellulose, or any combinations thereof, polyethylene, polypropylene, polybutylene, polystyrene, polyvinylchloride, polyacrylate, polymethacrylate, polyacrylonitrile, polyacrylamide, polyamide, nylon, polyimide, polyester, polycarbonate, polylactic acid, polyhydroxyalkanoate, ethylene vinyl acetate, polyurethane, silicone, thermoplastic starch, trans-poly isoprene, derivatives thereof, copolymers thereof, mixtures thereof, or any suitable smooth plastic material. Additives can be included in the material to alter or enhance certain material properties. Suitable additives include, for example, mold release agents, slip agents, surface energy modifiers, pearlescent agents, inorganic fillers, and/or any other suitable additives. The grip portion can be a same material as the barrel portion. Alternatively, the grip portion can be one or more different materials as compared to the barrel portion. The grip portion can also comprise one or more compressible materials, such as, e.g., rubber, silicone, and/or foam, and/or one or more soft plastics. The grip portion can have a substantially rigid inner surface and a deformable outer surface, such as, e.g., to improve user comfort while substantially preventing compression of the interior of the grip, such as, e.g., to allow the plunger to move in the axial direction while the outer surface of the grip is deformed by a user's fingers.

The plunger can be constructed from any suitable material. The barrel portion can be constructed from any suitable material. Suitable materials include, for example, paper, paperboard, cardboard, cellulose, such as, e.g., molded cellulose, or any combinations thereof, polyethylene, polypropylene, polybutylene, polystyrene, polyvinylchloride, polyacrylate, polymethacrylate, polyacrylonitrile, polyacrylamide, polyamide, nylon, polyimide, polyester, polycarbonate, polylactic acid, polyhydroxyalkanoate, ethylene vinyl acetate, polyurethane, silicone, thermoplastic starch, trans-poly isoprene, derivatives thereof, copolymers thereof, mixtures thereof, or any suitable smooth plastic material. Suitable plungers are disclosed in, e.g., U.S. Pat. Nos. 5,346,468 and 5,558,631. Additives can be included in the material to alter or enhance certain material properties. Suitable additives include, for example, mold release agents, slip agents, surface energy modifiers, pearlescent agents, inorganic fillers, and/or any other suitable additives.

The plunger can be hollow or solid. The plunger can have a hollow interior, a first end, and a second end opposed to the first end. The first end is the portion of the plunger that pushes against the tampon during the expulsion of the tampon from the barrel portion. The second end is the portion of the plunger in which the axial force is applied to expel the tampon from the barrel portion. The plunger can have a locking mechanism, such as, e.g., a locking mechanism that retains the plunger within the barrel portion and/or grip portion of the applicator prior to depression of the plunger and expulsion of the tampon. Examples of such locking mechanisms are described in, for example, U.S. Pat. Nos. 6,019,744 and 6,450,986.

The plunger can be an optional component for use with the applicator. For example, the applicator can be fully functional if the plunger is omitted, i.e., if a user must insert and push the feminine hygiene product through the tampon applicator digitally.

At least a portion of the applicator can contact and/or conform to at least a portion of the surface of the tampon. Rigid insertion end structures can be shaped in a suitable manner, such as, e.g., by injection molding, or by reshaping in a secondary process to provide at least a degree of profiled shape observation. Alternatively, insertion ends of applicators made from flexible or pliable materials, such as films, paper and flexible wovens or non-wovens, can also be used. Such flexible or pliable insertion ends include those which partially or fully enclose the tampon comprising a "sleeve" or a "tube," such as, e.g., in U.S. Pat. Nos. 2,922,422 and 2,922,423; a "sheath," such as, e.g., in U.S. Pat. Nos. 2,092,427 and 3,749,093; a "barrel," such as, e.g., in U.S. Pat. No. 5,135,475; a "bag," such as, e.g., in U.S. Pat. No. 3,358,686; or a "film enclosure," such as, e.g., in U.S. Pat. No. 4,610,659.

Figure 9:
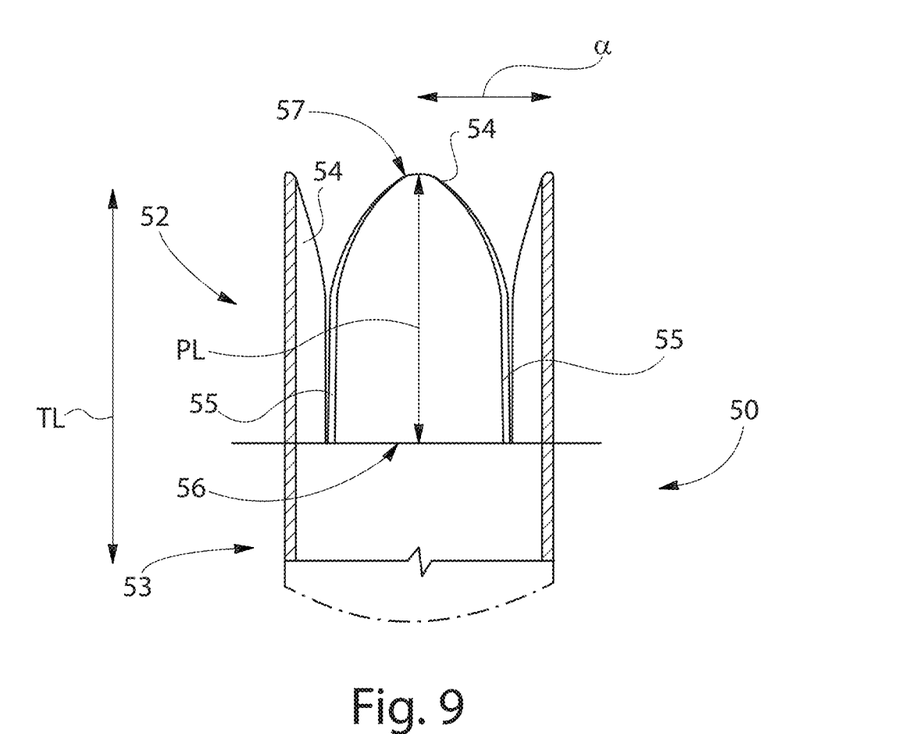
FIG. 9 shows a partial view of an applicator insertion end.

FIG. 9 shows a partial cross-section of an applicator barrel. The applicator barrel 50 includes an insertion tip 52 proximal a first end 53. A plurality of petals 54 is disposed about insertion tip 52. A slot 55 exists between adjacent petals. Each of petals 54 has a petal base 56 and a petal length PL extending from petal base 56 to the petal distal end 57. Insertion tip 52 has a tip length TL defined from a point 5 mm below petal bases 56 and extending to petal distal ends 57.

Insertion tip 52 has a tapering wall thickness along tip length TL defined by angle α. Some commercially-available applicators include a draft angle to aid in removing the applicator from a manufacturing mold, but these angles are generally small; for example, around 0.2 degrees. A wall thickness angle α in insertion tip 52 can be at least twice such a draft angle. For example, insertion tip 52 along tip length TL can have a wall thickness angle α of greater than or equal to 0.4 degrees, 0.5 degrees, 0.6 degrees, 0.7 degrees, 0.8 degrees, 1 degree, 2 degrees or more. Other wall thickness angles are contemplated by the present invention, even though they are not explicitly mentioned.

The insertion tip may comprise more than one angle. That is, the insertion tip may have a non-uniform taper along the tip length. For example and with reference to FIG. 5, applicator barrel 60 includes an insertion tip 62 that comprises a first angle β and a second, different angle λ along different sections of tip length TL. The two angles can differ in dimension from one another by 50% or more. The first angle β can be less than or equal to 0.3 degrees and second angle λ is greater than or equal to 0.4 degrees.

As noted in the background section, known applicator petals generally bend at the petal bases. Unique design approaches of the present invention permit the creation of one or more inflection or bending points at locations other than the petal bases. The design approaches provided by the present invention reduce and/or increase flexural resistance in targeted regions of the insertion tip. The wall thickness of the insertion tip can vary by at least 15%, 20%, or 25% over a 3 mm, 4 mm, or 5 mm section along the tip length to create a petal doming inflection point. This creates a step change in wall thickness. A thickness step change can be imparted via a single wall thickness angle with surrounding sections being devoid of a wall thickness taper, or via two or more angles. Petal inflection points of the present invention can exist proximal the petal bases. Petal inflection points can exist above the petal bases; for example, at least 1 mm, at least 2 mm, or at least 3 mm above the petal bases. Petal wall thickness can also vary circumferentially along the width of the petals.

Pessary Expulsion Force Test

The expulsion force can be measured by using a Pessary Expulsion Force Test. The Pessary Expulsion Force Test determines the force characteristics of pessary expulsion from an applicator. The test can utilize a constant rate of elongation tensile tester with a load cell chosen such that the measure force is between 10% and 90% of the cell's capacity. The test can also utilize an applicator fixture that must be able to hold applicator vertically downward (petals facing down) while exerting minimal force to the axial portion of the applicator.

The tester and fixture is placed in a room with a temperature of 21° C. (±4° C.). This uniform temperature allows for comparison between products that expand based on temperature.

Sample Preparation (if Needed):

A test sample is prepared by removing any outer wrapper that may exist and tucking any out-hanging withdrawal cord inside the applicator pusher.

The applicator is placed into fixture such that the lip of the applicator is being held up (opposite to the direction of testing, preventing applicator from falling through the fixture). The fixture is then oriented within the tensile tester setup such that the direction of the force of the tensile tester should follow the long direction of the applicator and be applied directly on the pusher (plunger). The test is then run (speed: 1 mm/sec, data acquisition 20 hz) where the tensile tester is exerting downward force directly on the pusher such that the pessary moves toward and out of the petals. Test is complete when the body of the pessary has been completely expelled from the applicator.

Reporting of the results includes obtaining the force vs extension curves and determining the maximum expulsion force, as well as the number of peaks in the curve, at what displacements they occurred and the corresponding loads. Examples of reported results are found on FIGS. 6-8.

The pessary device can be used daily. For example, a user can insert the pessary device, wear the pessary device for a suitable wear time, such as, for example, up to 4 hours, up to 5 hours, up to 6 hours, up to 7 hours, up to 8 hours, up to 9 hours, up to 10 hours, up to 11 hours, or up to 12 hours, or more, remove the pessary device, dispose of the pessary device, and insert a new pessary device.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Values disclosed herein as ends of ranges are not to be understood as being strictly limited to the exact numerical values recited. Instead, unless otherwise specified, each numerical range is intended to mean both the recited values and any integers within the range. For example, a range disclosed as "1 to 10" is intended to mean "1, 2, 3, 4, 5, 6, 7, 8, 9, and 10."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An intravaginal pessary device housed within an applicator, wherein the applicator comprises a barrel region with an insertion end, the insertion end comprising a containment element, the containment element comprising at least one petal that holds the pessary device within the barrel region, wherein the pessary device and the applicator are configured such that they exhibit a maximum expulsion force that is greater than 0 and less than 1500 grams-force, and wherein the pessary device and the applicator exhibit an expulsion force profile that has a two peak structure with a first peak occurring proximate commencement of application of expulsion force, a second peak occurring proximate completion of the application of the expulsion force, wherein the first and second peaks are the highest two peaks of the force profile, neither peak exceeds 4 Newtons, the second peak is a percentage of the first peak, and the area between the two peaks drops to below 2 Newtons; wherein the maximum expulsion force is at least in part a force required to open the at least one petal and thereby urge the pessary device through the insertion end of the applicator.

2. The pessary device and applicator of claim 1, wherein the pessary device has a maximum lateral dimension, wherein the maximum lateral dimension is located closer to a top or bottom of the pessary device than to a mid-section of the pessary device.

3. The pessary device and applicator of claim 1, wherein the barrel region has an inner lateral dimension and the pessary device has a maximum lateral dimension and the inner lateral dimension of the barrel region is greater than the maximum lateral dimension of the pessary device.

4. The pessary device and applicator of claim 3, wherein the barrel region is circular in cross section and the inner lateral dimension is an inner diameter of the barrel region.

5. The pessary device and applicator of claim 4, wherein the pessary device at the maximum lateral dimension is circular in cross section and the maximum lateral dimension is a maximum diameter of the pessary device.

6. The pessary device and applicator of claim 1, wherein the pessary device has a length between 35 mm and 60 mm and the maximum lateral dimension is greater than 10 mm and less than 35 mm.

7. The pessary device and applicator of claim 1, wherein the pessary device has a weight greater than 1 gram and less than 10 grams.

8. The pessary device and applicator of claim 1, wherein the pessary device and the applicator require greater than 0 Newtons per mm and less than 1000 Newtons per mm average to expel the pessary device.

9. The pessary device and applicator of claim 1, wherein the applicator barrel has an inner diameter greater than 5 mm and less than 22 mm.

10. The pessary device and applicator of claim 1, wherein the pessary device is in the shape of an hourglass, a waisted cylinder, a figure-8 or a peanut.

11. The pessary device and applicator of claim 1, wherein the pessary device comprises a convex portion and a concave portion, and wherein the convex portion provides more resistance to expulsion force than the concave portion.

* * * * *